United States Patent [19]

Gross et al.

[11] Patent Number: 4,781,723

[45] Date of Patent: Nov. 1, 1988

[54] COMPOSITIONS FOR THE GROOMING OF HAIR

[75] Inventors: Paul Gross, Darmstadt; Udo Wiegand, Weiterstadt, both of Fed. Rep. of Germany

[73] Assignee: Wella Aktiengesellschaft, Darmstadt, Fed. Rep. of Germany

[21] Appl. No.: 12,666

[22] PCT Filed: Jun. 21, 1986

[86] PCT No.: PCT/EP86/00364

§ 371 Date: Jan. 27, 1987

§ 102(e) Date: Jan. 27, 1987

[87] PCT Pub. No.: WO87/00041

PCT Pub. Date: Jan. 15, 1987

[51] Int. Cl.$^4$ .......................... A61K 7/06; A61K 7/11; A61K 7/13

[52] U.S. Cl. .......................... 8/405; 8/426; 8/429; 424/47; 424/70; 424/71

[58] Field of Search .................. 424/70, 71, 47; 8/429, 8/405, 426

[56] References Cited

U.S. PATENT DOCUMENTS

| | | | |
|---|---|---|---|
| 3,954,960 | 4/1976 | Valan | 424/47 |
| 3,958,581 | 5/1976 | Abegg et al. | 132/7 |
| 4,009,256 | 2/1977 | Nowax, Jr. et al. | 424/70 |
| 4,223,009 | 9/1980 | Chakrabarti | 424/47 |
| 4,240,450 | 12/1980 | Grollier et al. | 132/7 |
| 4,391,286 | 7/1983 | Hsiung et al. | 132/7 |
| 4,445,521 | 5/1984 | Grollier et al. | 132/7 |

FOREIGN PATENT DOCUMENTS

| | | |
|---|---|---|
| 5329941 | 3/1978 | Japan . |
| 2063671 | 6/1981 | United Kingdom . |
| 02999 | 7/1985 | World Int. Prop. O. . |

OTHER PUBLICATIONS

Schönfeldt, N. *Surface Active Ethylene Oxide Adducts* Pergamon Press, NY 1969 pages 343, 346.

*Primary Examiner*—Paul Lieberman
*Assistant Examiner*—Linda D. Skaling
*Attorney, Agent, or Firm*—Michael J. Striker

[57] ABSTRACT

Compositions for the grooming of hair based on a synergistic combination of (a) 0.01 to 0.09 percent by weight of a quaternized copolymer of vinyl pyrrolidone and dimethylaminoethylmethacrylate (80:20) and (b) 0.01 to 0.5 percent by weight tetraoxyethylene lauryl ether.

It is shown through corresponding tests that fatty alcohol polyoxyethylene eithers other than tetraoxyethylene lauryl ether with the components (a) show no synergistic increase in effect with respect to the improvement of ease of combing when wet, luster, feel and static electric charge of the hair.

7 Claims, No Drawings

COMPOSITIONS FOR THE GROOMING OF HAIR

DESCRIPTION

The subject matter of the invention is compositions for the grooming of hair which need not be rinsed out and which contain tetraoxyethylene lauryl ether and a quaternized copolymer of vinyl pyrrolidone with dimethylaminoethyl-methacrylate (80:20).

Hair care compositions are used for improving the condition of the hair and are usually oil-in-water emulsions which contain oily, semisolid or solid substances, for instance, paraffin oil, vaseline, wool fat, wool fat alcohol, fatty acid ester and hydrocarbon waxes, as framework components. Normally, quaternary ammonium compounds such as oxyethylated alkyl ammonium phosphates, alkyl trimethylammonium chlorides, dialkyl dimethyl ammonium chlorides, alkyl dimethylbenzyl ammonium chlorides and alkyl pyridinium chlorides are used alone or in combination with nonionogenic emulsifiers as emulsifiers for such emulsions. Aqueous solutions and aqueous gels with a quaternary ammonium compound content are also frequently used as hair care compositions.

The aforementioned monomeric quaternary compounds serve at the same time to improve the ease of combing when wet and the feel, particularly of damaged hair.

However, such additions of quaternary ammonium compounds impair the physiological compatibility of such preparations, particularly the eye's tolerance to them.

It has now been found, however, that a surprising and outstanding improvement in the ease of combing of hair is brought about by means of compositions for the grooming of hair based on an aqueous, alcoholic or aqueous-alcoholic solution of a quaternized copolymer and an oxyethylated fatty alcohol, as well as possible propellants and other additions, characterized in that they contain (a) 0.01 to 0.09 percent by weight quaternized copolymer of vinyl pyrrolidone and dimethylaminoethyl-methacrylate (80:20) as film forming resin and (b) 0.01 to 0.5 percent by weight tetraoxyethylene lauryl ether as oxyethylated fatty alcohol.

The copolymer of vinyl pyrrolidone and dimethylaminoethylmethacrylate mentioned in (a) is preferably quaternized with dimethyl sulfate or diethyl sulfate. The commercial products GAFQUAT® 734 AND GAFQUAT® 755 of the GAF Corporation, New York, are suitable as the quaternized copolymer of vinyl pyrrolidone and dimethylaminoethylmethacrylate (80:20). They have the following formula:

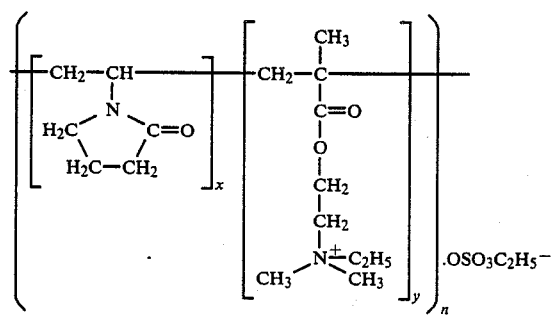

(ratio x:y = 80:20)

In GAFQUAT® 755N the average molecular weight is approximately 1,000,000 (g/moles) and, in GAFQUAT® 734, approximately 100,000 (g,moles).

Tetraoxyethylene lauryl ether of the formula $$CH_3(CH_2)_{10}CH_2(OCH_2CH_2)_4OH$$

is the tetraoxyethylene ether of the lauryl alcohol.

In the compositions according to the invention, the tetraoxyethylene lauryl ether is contained in a quantity of 0.01 to 0.5 percent by weight, preferably 0.03 to 0.09 percent by weight. The content of quaternized copolymer of vinyl pyrrolidone and dimethylaminoethylmethacrylate is 0.01 to 0.09 percent by weight, preferably 0.03 to 0.07 percent by weight. Ethyl alcohol and isopropyl alcohol, or mixtures of these two alcohols, can be contained in the compositions, according to the invention, in quantities of 0 to 99.98 percent by weight. Of course, other cosmetic additions for hair, such as perfume oil, herbal extracts, bactericides or fungicides, anti-dandruff agents and dissolving intermediaries for perfume oil, can also be contained in the compositions according to the invention, insofar as such additions appear useful and advisable. Furthermore, tinting dyes for tinting the preparation of dyes to be absorbed directly by the hair in order to simultaneously shade the hair can also be contained.

Of the latter dyes, which can be present individually or in combination, the following classes are mentioned by way of example: aromatic nitro dyes, e.g. 1,4-diamino-2-nitrobenzene, azo dyes, e.g. Acid Brown 4 (C.I. No. 14 805), anthraquinone dyes, e.g. Disperse Violet 4 (C.I. No. 61 105) and triphenylmethane dyes, e.g. Basic Violet 1 (C.I. No. 42 535), wherein the dyes of these classes can have an acidic, nonionogenic or basic character, depending on their type of substituents. The total concentration of the latter is usually approximately 0.05 to 2.0 percent by weight.

The compositions, according to the invention, can also be put into a container under pressure with the addition of a propellant, wherein the preparation is discharged as foam and can be easily dispensed and distributed in the hair by means of a valve provided with an application nozzle. Suitable propellants are, e.g. readily volatile fluorochloric hydrocarbons such as difluorodichloromethane, trichloromonofluoromethane, tetrafluorodichlorethane or lower alkanes such as n-butane, i-butane and propane or, also, dimethylether as well as propellants which are in gaseous form under the respective pressure, such as $N_2$, $N_2O$ and $CO_2$. The propellants are advisably contained in these compositions in a quantity of approximately 2 to 10 percent by weight.

The compositions, according to the invention, are applied—normally after the hair is washed—to the towel-dried hair in a quantity of approximately 5 to 15 g, according to the fullness of the hair. Next, the hair is combed through and then dried.

Normally, hair care compositions which are in the form of emulsions or aqueous gels are rinsed out of the hair again with water after being allowed to act for a period of several minutes. If they remained in the hair the hair would be sticky and therefore unusable for styling. For this reason it is a particular advantage of the compositions, according to the invention, that they can remain in the hair without being rinsed out. The user is thus spared the time and effort of rinsing out.

The observed outstanding improvement in the ease of combing the hair is surprising and can only be explained by means of synergism, since the tetraoxyethylene lauryl ether or the quaternized copolymer of vinyl pyrrolidone and dimethylaminoethylmethacrylate applied to the hair alone in an appropriate solution (see test examples C and D) brings about only a moderate and unsatisfactory improvement of the criteria mentioned there.

In addition, the following test examples E, F, G and H proved that fatty alcohol polyoxyethylene ethers other than tetraoxyethylene lauryl ether do not have the synergistic effect required for use in the compositions according to the invention.

Because of their outstanding effect in improving the ease of combing, the use of the abovementioned quaternary ammonium compounds is entirely unnecessary in the compositions for the grooming of hair, according to the invention, unless they are added to the compositions in small concentrations of up to approximately 0.2 percent by weight as preservatives for achieving bactericidal or fungicidal characteristics.

The following examples explain the subject matter of the invention in more detail.

EXAMPLES

EXAMPLE 1

Composition in the form of an aqueous solution

| | |
|---|---|
| 0.08 g | tetraoxyethylene lauryl ether |
| 0.06 g | copolymer of vinyl pyrrolidone and dimethyl-aminoethylmethacrylate in a ratio of 80:20, quaternized with diethyl sulfate |
| 99.86 g | water, completely softened |
| 100.0 g | |

EXAMPLE 2

Composition in the form of an aqueous-alcoholic solution

| | |
|---|---|
| 0.06 g | tetraoxyethylene lauryl ether |
| 0.05 g | copolymer of vinyl pyrrolidone and dimethyl-aminoethylmethacrylate in a ratio of 80:20, quaternized with diethyl sulfate |
| 15.00 g | ethanol |
| 84.89 g | water, completely softened |
| 100.0 g | |

EXAMPLE 3

Composition in the form of compressed gas packing

| | |
|---|---|
| 0.09 g | tetraoxyethylene lauryl ether |
| 0.07 g | copolymer of vinyl pyrrolidone and dimethyl-aminoethylmethacrylate in a ratio 80:20, quaternized with diethyl sulfate |
| 2.50 g | isopropanol |
| 97.34 g | water, completely softened |
| 100.0 g | | filling:
96.0 g liquid of the aforementioned composition
2.8 g propane
1.2 g butane

EXAMPLE 4

Composition in the form of compressed gas packing

| | |
|---|---|
| 0.08 g | tetraoxyethylene lauryl ether |
| 0.06 g | copolymer of vinyl pyrrolidone and dimethyl-aminoethylmethacrylate in a ratio of 80:20, quaternized with diethyl sulfate |
| 2.50 g | ethanol |
| 97.36 g | water, completely softened |
| 100.0 g | | filling:
96.0 liquid of the aforementioned composition
2.0 g propane
1.6 g butane
0.4 g dimethyl ether

EXAMPLE 5

Composition in the form of an aqueous-alcoholic solution

| | |
|---|---|
| 0.09 g | tetraoxyethylene lauryl ether |
| 0.07 g | copolymer of vinyl pyrrolidone and dimethyl-aminoethylmethacrylate in a ratio of 80:20, quaternized with diethyl sulfate |
| 0.03 g | Basic Violet 1 (C.I. No. 42 535) |
| 2.50 g | ethanol |
| 97.31 g | water, completely softened |
| 100.00 g | |

All percentages given in the present application are percent by weight.

TEST EXAMPLES

Test example A

After washing the hair beforehand, the towel-dried hair of 15 test persons was treated with a composition according to example 1. Five of the test persons had normal hair. The remaining ten persons had hair ranging from damaged to badly damaged. In order to obtain clear results and to compensate for diverging hair qualities from one test person to another the hair was parted in the middle and 2.5 to 7.5 g of the composition was applied to one half of the hair, depending on the fullness of the hair, while the other half remained untreated. Next, each half of the hair was combed through separately, then dried and styled. In this way the effect of the preparation could be judged in a decisive manner by a group of experts in the field of hairstyling. An evaluation was made according to the model for the combined criteria of ease of combing when wet, curliness, luster, feel and static electric charge of the hair:

Grade:
1=very good
2=good
3=satisfactory
4=unsatisfactory

The following table 1 shows the results of the test for the half of the hair treated in this manner in comparison to the untreated hair.

TABLE 1

| | Grade 1 | Grade 2 | Grade 3 | Grade 4 |
|---|---|---|---|---|
| Number of test persons | 12 | 2 | 1 | 0 |

Test example B

The hair of another group of 17 test persons was treated with a composition according to example 3 in the same manner as in test example A. Ten persons in the group had hair ranging from damaged to badly damaged. The remaining 7 persons had normal hair. The results of this test are comprised in the following table 2.

TABLE 2

|  | Grade 1 | Grade 2 | Grade 3 | Grade 4 |
|---|---|---|---|---|
| Number of test persons | 13 | 3 | 1 | 0 |

Test example C

In order to check the synergistic effect the hair of another test group of 14 persons was treated on one side with a composition according to example 1, as described in test example A, but the tetraoxyethylene lauryl ether was replaced with the corresponding quantity of water. The other half of the hair remained untreated. 4 test persons had normal hair and 10 persons had damaged hair. The test results are shown in table 3.

TABLE 3

|  | Grade 1 | Grade 2 | Grade 3 | Grade 4 |
|---|---|---|---|---|
| Number of test persons | 0 | 2 | 6 | 6 |

Test example D

In order to further check the synergistic effect a fourth test group of 12 persons, of whom 4 had normal hair and 8 had badly damaged hair, were treated on one half of their hair with a composition according to example 1 in the same way as in test example A, but the composition contained no quaternized copolymer of vinyl pyrrolidone and dimethylaminoethylmethacrylate (80:20). In the composition according to example 1 the quaternized copolymer was replaced with the corresponding weight proportion of water. The second half of the hair remained untreated. The result of the test is shown in the following table 4.

TABLE 4

|  | Grade 1 | Grade 2 | Grade 3 | Grade 4 |
|---|---|---|---|---|
| Number of test persons | 0 | 3 | 3 | 6 |

A comparison of tables 1 or 2 with table 3 and table 4 clearly shows that the combination contained in the compositions according to the invention have a synergistic effect in comparison with the effect of the individual components.

Test example E

The hair of a test group of 10 persons with hair ranging from damaged to badly damaged was treated on one side in a manner analogous to test example A with a preparation composition according to example 1, but one in which the tetraoxyethylene lauryl ether was replaced with the same quantity of trioxyethylene stearyl ether. The other side of the hair remained untreated. The following table 5 shows the test results.

TABLE 5

|  | Grade 1 | Grade 2 | Grade 3 | Grade 4 |
|---|---|---|---|---|
| Number of test persons | 0 | 1 | 7 | 2 |

Test example F

The hair of a group of 9 test persons with hair ranging from damaged to badly damaged was treated on one side with a preparation composition according to example 1 in a manner analogous to test example A, but one in which the tetraoxyethylene lauryl ether was replaced with the same quantity of isostearic alcohol, ethoxylated with 10 moles ethylene oxide. The other side of the hair remained untreated. The following table 6 shows the result of the test.

TABLE 6

|  | Grade 1 | Grade 2 | Grade 3 | Grade 4 |
|---|---|---|---|---|
| Number of test persons | 0 | 1 | 3 | 5 |

The following test examples G and H show that of the polyoxyethylene lauryl ethers only tetraoxyethylene lauryl ether has a clear synergistic effect.

Test example G

Another group of 10 test persons with hair ranging from damaged to badly damaged was treated on one side in a manner analogous to test example A with a composition according to example 1, but one in which the tetraoxyethylene lauryl ether was replaced with an identical quantity of trioxyethylene lauryl ether. The other side of the hair remained untreated. The following table 7 shows the result of the test.

TABLE 7

|  | Grade 1 | Grade 2 | Grade 3 | Grade 4 |
|---|---|---|---|---|
| Number of test persons | 0 | 4 | 5 | 1 |

Test example H

A test group of 10 persons with damaged to badly damaged hair were likewise treated on one side of the hair with a composition according to example 1 in a manner analogous to test example A, but one in which the tetraoxyethylene lauryl ether was replaced with an equal quantity of pentaoxyethylene lauryl ether. The other side of the hair remained untreated.

The following table 8 shows the test results.

TABLE 8

|  | Grade 1 | Grade 2 | Grade 3 | Grade 4 |
|---|---|---|---|---|
| Number of test persons | 0 | 2 | 6 | 2 |

The results of the preceding tests show that fatty alcohol polyoxyethylenes other than tetraoxyethylene lauryl ether are unsuitable for use according to the invention.

The surprising and outstanding synergistic improvement of the hair conditioning characteristics, particularly with badly damaged hair, is limited in the described test results to the combination of tetraoxyethylene lauryl ether with a quaternized copolymer of vinyl pyrrolidone and dimethylaminoethylmethacrylate (80:20), according to the invention, and can not be achieved with other fatty alcohol polyoxyethylene ethers.

We claim:

1. A synergistically effective hair-grooming composition, which once applied, need not be removed from the hair by rinsing, which comprises:
    (a) 0.01 to 0.09% by weight of a quaternized copolymer of vinylpyrrolidone and dimethylaminoethylmethacrylate in a molar ratio of 80 to 20;
    (b) 0.01 to 0.5% by weight of tetraoxyethylene lauryl ether; and
    (c) water, an alcohol selected from the group consisting of ethanol, isopropanol, and mixtures thereof, or a mixture of water and the alcohol.

2. The synergistically effective hair-grooming composition defined in claim 1 wherein the quaternized copolymer of vinylpyrrolidone and dimethylaminoethylmethacrylate is quaternized with dimethyl- or diethylsulfate, and present in the composition in an amount of 0.03 to 0.07%.

3. The synergistically effective hair-grooming composition defined in claim 1 wherein the tetraoxyethylene lauryl ether is present in an amount of 0.03 to 0.09%.

4. The synergistically effective hair-grooming composition defined in claim 1 which further comprises 0.05 to 2% by weight of a dye which is directly absorbed into the hair for the purpose of simultaneously tinting the hair.

5. The synergistically effective hair-grooming composition defined in claim 4 in that the dye which is directly absorbed into the hair is selected from the group consisting of an aromatic nitro dye, an azo dye, an anthraquinone dye, and a triphenylmethane dye.

6. The synergistically effective hair-grooming composition defined in claim 1 which further comprises 2 to 10% by weight of a propellant selected from the group consisting of: n-butane, isobutane, propane, difluorodichloromethane, trichloromonofluoromethane, tetrafluorodichloroethane, dimethylether, $N_2$, $N_2O$ and $CO_2$.

7. A process for grooming hair to improve ease of combing, luster, feel, and static electric charge, by employing a synergistically effective hair-grooming composition, which once applied, need not be removed from the hair by rinsing, which comprises the steps of:
    (1) washing the hair;
    (2) towel-drying the hair;
    (3) applying to the hair having been previously washed and towel-dried, 5 to 15 g of a synergistically effective, aqueous, alcoholic, or aqueous alcoholic composition for grooming the hair which comprises:
        (a) 0.01 to 0.09% by weight of a quaternized copolymer of vinylpyrrolidone and dimethylaminomethyl-ethacrylate in a molar ratio of 80 to 20;
        (b) 0.01 to 0.5% weight of tetraoxyethylene lauryl ether; and
        (c) water, an alcohol selected from the group consisting of ethanol, isopropanol, and mixtures thereof, or a mixture of water and the alcohol;
    (4) combing the hair; and
    (5) without previously rinsing the hair, drying the hair thereby allowing said synergistic composition for grooming the hair to remain in the hair.

* * * * *